US00PP14420P29

(12) United States Plant Patent
Byrnes

(10) Patent No.: US PP14,420 P2
(45) Date of Patent: Dec. 23, 2003

(54) JAPANESE HOLLY PLANT NAMED 'DROPS OF GOLD'

(50) Latin Name: *Ilex crenata*
Varietal Denomination: Drops of Gold

(75) Inventor: Ronald W. Byrnes, Geneva, OH (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/327,923

(22) Filed: Dec. 26, 2002

(51) Int. Cl.[7] ..... A01H 5/00
(52) U.S. Cl. ..... Plt./247

(58) Field of Search ..... Plt./247

*Primary Examiner*—Kent Bell
(74) *Attorney, Agent, or Firm*—Burns, Doane, Swecker & Mathis, L.L.P.

(57) ABSTRACT

A new variety of *Ilex crenata* plant is provided that is well suited for growing as attractive ornamentation in the landscape. The new variety is believed to be a spontaneous mutation of unknown causation of the 'Hetzii' variety (non-patented in the United States). The foliage of the new variety is particularly distinctive and when exposed to full sun during its formation is dark glossy green with irregular bright golden yellow variegation. An attractive broad upright spreading growth habit is displayed. Dioecious female function flower are formed. Good hardiness is displayed in U.S.D.A. Hardiness Zone No. 6a.

5 Drawing Sheets

Figure 1:
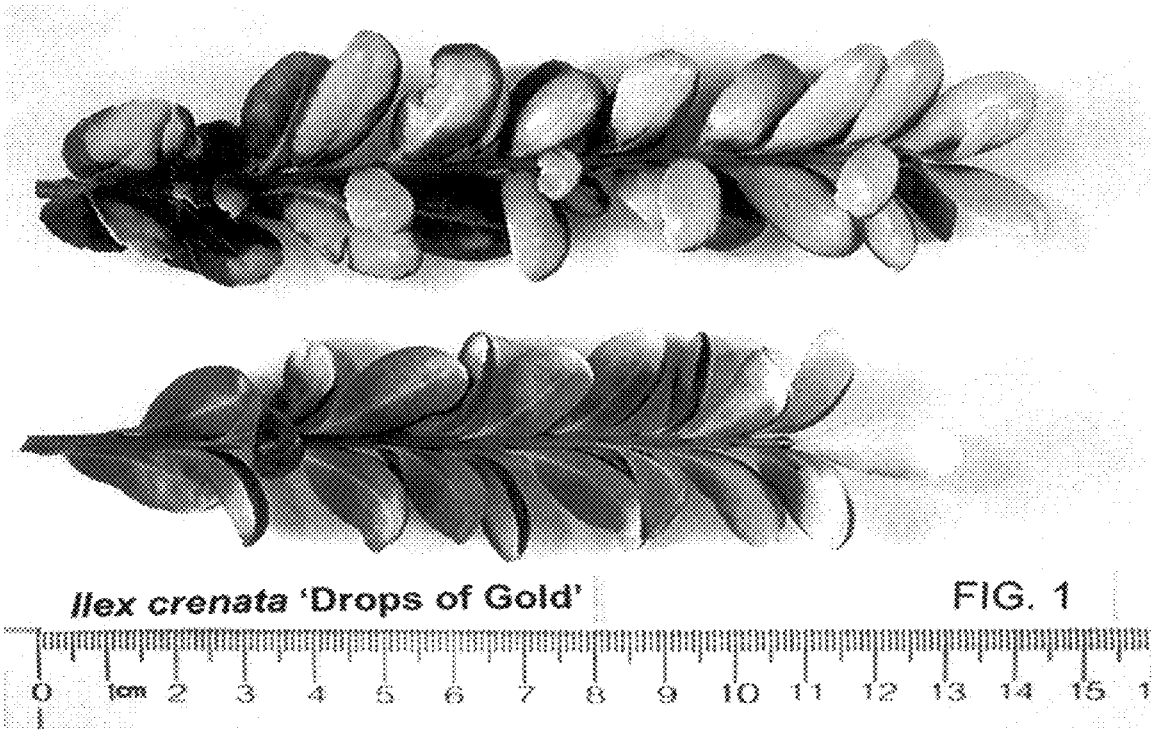

Botanical/commercial classification: *Ilex crenata* / Japanese Holly Plant.
Varietal denomination: cv. 'Drops of Gold'.

SUMMARY OF THE INVENTION

The new variety of the present invention is a distinctive variegated sport of *Ilex crenata*, 'Hetzii' (non-patented in the United States). Holly plants of this species sometimes are known as Japanese Holly.

A single plant of the new variety was discovered during November 1987 while growing in a block of *Ilex crenata* 'Hetzii' plants in a cultivated area of my nursery at Geneva, Ohio. This new variety is believed to be a spontaneous mutation of unknown causation. I was attracted to the new variety in view of its distinctive combination of characteristics. Had the new variety not been discovered and preserved by me it would have been lost to mankind.

It was found that the new Japanese Holly variety of the present invention exhibits the following combination of characteristics:

(a) when exposed to full sun during formation the foliage is dark glossy green with irregular bright golden yellow variegation that is absent in the parent 'Hetzii' variety, (b) exhibits an attractive broad upright spreading growth habit, (c) forms dioecious female functional flowers, and (d) has proven to be hardy in U.S.D.A. Hardiness Zone No. 6A.

It has been observed that brightest foliage variegation is manifest when the new growth emerges and matures in full sun. Some leaves are completely bright golden yellow in coloration when growth occurs in full sun. When shoots are formed and mature in more shaded areas they commonly do not show the yellow variegation even when subsequently exposed to full fun.

The new variety of the present invention can be readily distinguished from its 'Hetzii' parent variety by the presence of the illustrated distinctive variegation of the leaves. Such variegation is totally lacking on the 'Hetzii' variety.

A five year-old plant of the variety has been observed to exhibit a height of approximately 18 inches and a width of approximately 24 to 32 inches. The maximum plant dimensions for the new variety are unknown. However, it is estimated that a fully mature height of approximately 5 to 7 feet and width of approximately 10 to 12 feet likely will be achieved by the new variety. Plants of the new variety tend to grow rapidly immediately following asexual propagation.

The new variety of the present invention well meets the needs of the horticultural industry and can be grown in full sun to provide distinctive ornamentation. For instance, it can be grown to advantage as a colorful low hedge or as a specimen or container plant in the landscape.

The new variety of the present invention has been asexually reproduced by the use of terminal hardwood cuttings taken in November or early December at West Grove, Pa. and at Geneva, Ohio. It has been demonstrated that the unique combination of characteristics is firmly established and is transmitted to successive generations following such asexual propagation.

The new variety has been named 'Drops of Gold.'

BRIEF DESCRIPTION OF THE PHOTOGRAPHS

The accompanying photographs show typical specimens of the new variety while growing at West Grove, Pa. in color as nearly true as it is reasonably possible to make the same in color illustrations of this character. The photographs were taken during the late fall of 2002. The illustrated five year-old plant was growing on its own roots in a container in a nursery in an unheated tunnel structure that was completely open to the environment from early April through mid-November, and was covered with translucent white polyethylene sheeting from mid-November to early April. The illustrated two year-old plant was grown in a greenhouse until late May and then was transferred to the same unheated tunnel structure. The reduced expression of the yellow variegation on shoots of the two year-old plants can be attributed to their initial development under a lower light environment in a greenhouse just prior to moving to the higher light environment where they assumed more variegation prior to reaching maturity. Dimensions in centimeters are indicated at the bottom of each photograph.

FIG. 1—Illustrates specimens of mature current season terminal shoots of the five year-old plant. The top shoot displays a ventral (upper) view, and the lower shoot displays a dorsal (under) view.

Figure 2:
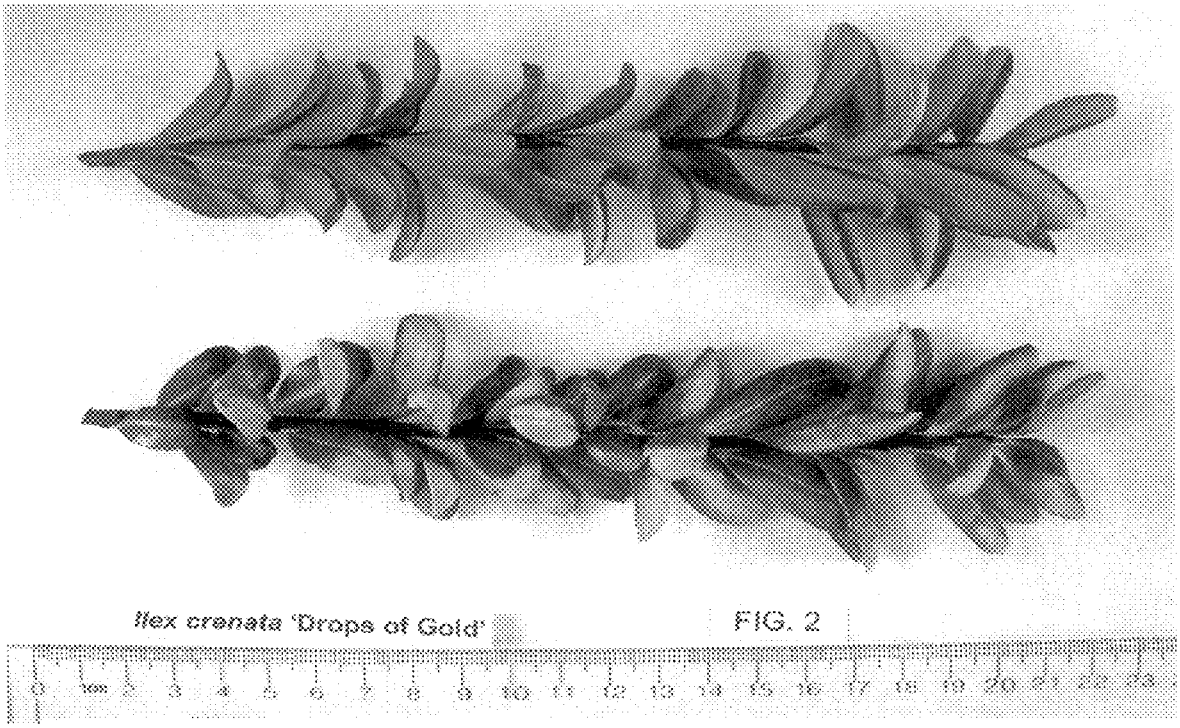

FIG. 2—Illustrates specimens of mature current season terminal shoots of the two year-old plant. The top shoot displays a ventral (upper) view, and the lower shoot displays a dorsal (under) view.

Figure 3:
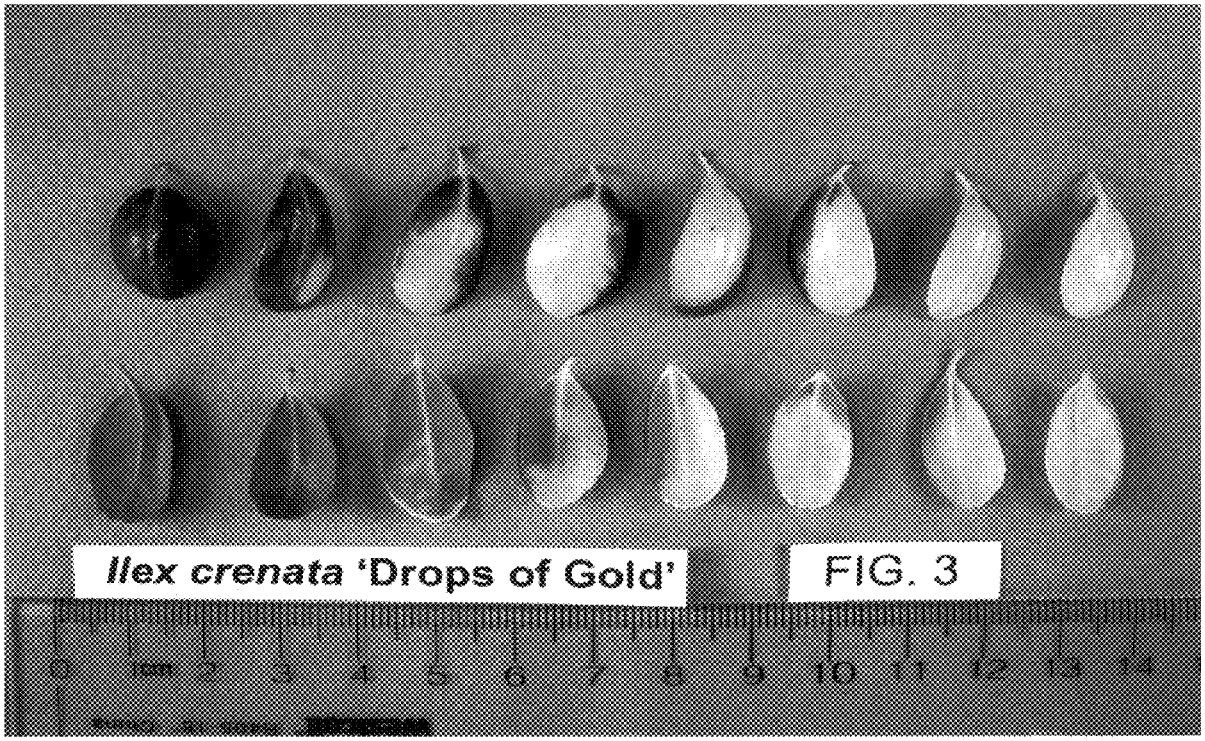

FIG. 3—Illustrates specimens of current season mature leaves of the five year-old plant. The upper row of leaves displays ventral (upper) views and the lower row of leaves displays dorsal (under) views.

Figure 4:
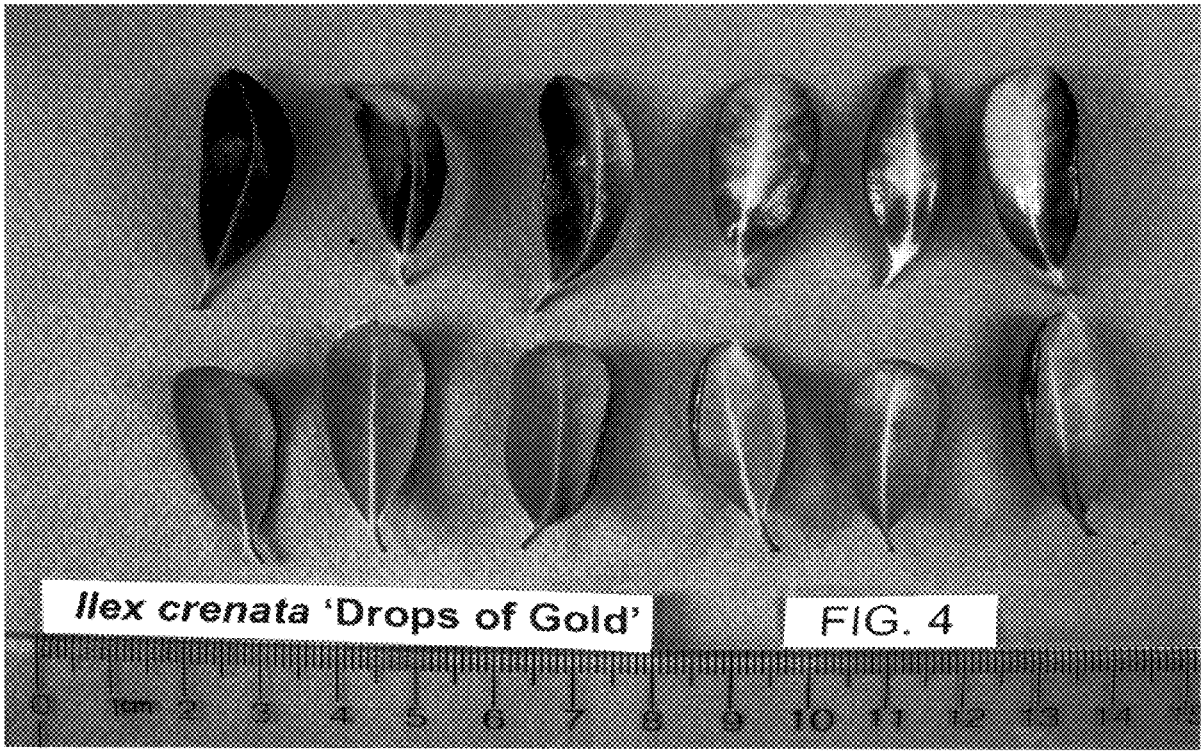

FIG. 4—Illustrates specimens of current season mature leaves of a two year-old plant. The upper row of leaves displays ventral (upper) views and the lower row of leaves displays dorsal (under) views.

Figure 5:
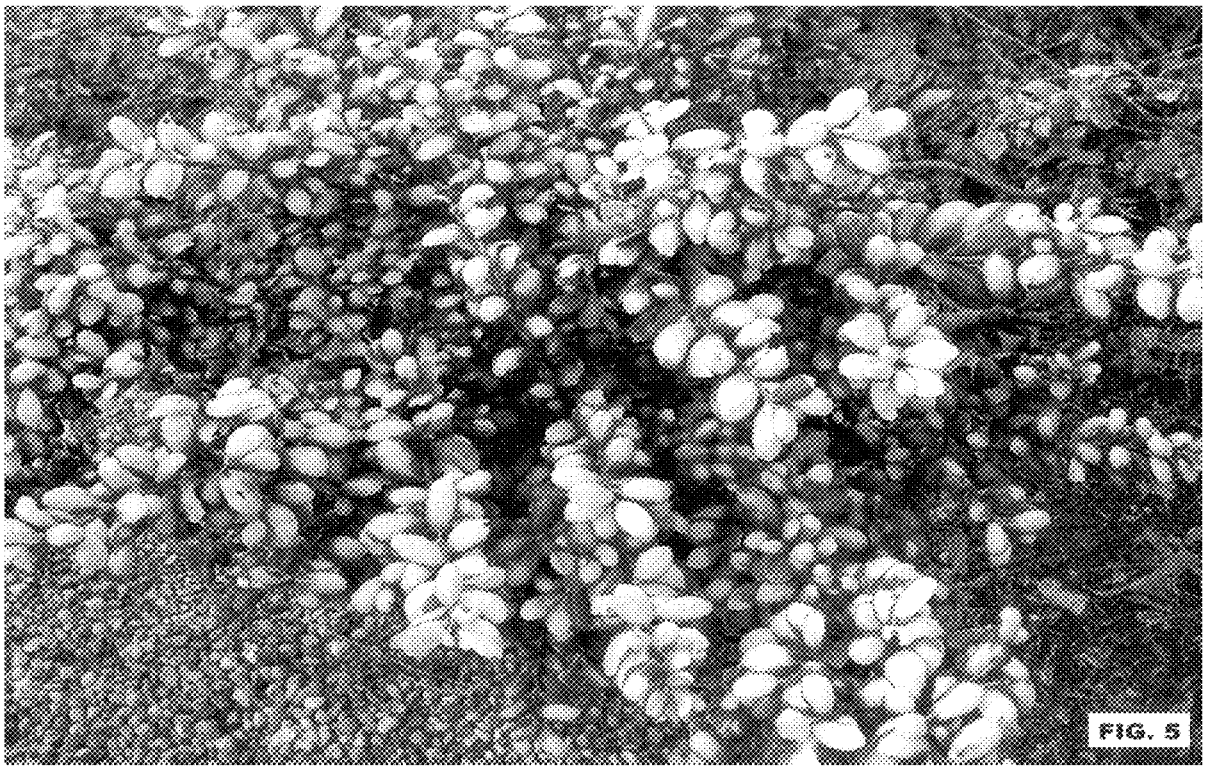

FIG. 5—Illustrates a specimen of the top canopy of shoots of the five year-old plant which was grown in full sun during the summer.

DETAILED DESCRIPTION

The following is a detailed description of the new variety that was obtained while observing the plants that are illustrated in the photographs. Such plants had been propagated by the use of hardwood cuttings and were growing except were otherwise indicated in containers at West Grove, Pa. while present in the tunnel structure where they were fully exposed to the environment from early April through mid-November, and were covered with white polyethylene sheeting during the winter. The plants received no supplemental heating. The chart used in the identification of color is The R.H.S. Colour Chart of The Royal Horticultural Society, London, England. Common color terms are to be accorded their customer dictionary significance. The inflorescence information was obtained at Geneva, Ohio on Jul. 1, 2002.

Botanical classification: *Ilex crenata*, cv. 'Drops of Gold'.

*Parent.*—'Hetzii' variety (non-patented in the United States).

Plant:

*Type.*—Hardy evergreen shrub for garden decoration and general landscape use.

*Growth habit.*—Broad, upright spreading and broader than tall.

*Height.*—Approximately 18 inches at an age of five years.

*Width.*—Approximately 24 to 32 inches at an age of five years.

Leaves:

*Type.*—Evergreen, broad, and simple.

*Blade length.*—Approximately 17.5 to 36.5 mm with an average of approximately 25.2 mm.

*Blade width.*—Approximately 9.75 to 14.0 mm with an average of approximately 11.98 mm.

*Petiole.*—Approximately 2.0 to 4.5 mm in length with an average of approximately 3.4 mm. Approximately 0.8 to 1.1 mm in diameter with an average of approximately 0.95 mm.

*Margins.*—Crenate, serrate, and revolute.

*Apex.*—Broadly obtuse (rounded), and mucronate.

*Base.*—Narrowly cuneate.

*Texture.*—Coriaceous.

*Arrangement.*—Alternate.

*Venation.*—Pinnately veined.

*Color.*—Mature Foliage (Five Year-Old Plant) Upper (Ventral) Surface: The all-green leaves and the distinctly green areas most distant from the yellow areas of the variegated foliage are near and through Green Group 139A to near and through Yellow-Green Group 147A. Approaching the areas of yellow variegation the green coloration is near and through Green Group 137A to 137B to Yellow-Green Group 146A to 146D. The variegated areas range from near and through Yellow-Green Group 153D to Yellow Group 9A and 9B in the darker areas, and Yellow Group 5D, 6D, 8C, 9A, 9B, 10A, 10B and 11A in lighter areas. Under (Dorsal) Surface: The all-green leaves and the distinctly green areas most distant from the yellow areas of the variegated foliage are near Yellow-Green Group 146B to 146C. The variegated areas range from near Yellow Group 8C to near and through Yellow Group 10B, 10C, and 11B. Mature Foliage (Two Year-Old Plant): Upper (Ventral) Surface: The all green leaves and the distinctly green areas most distant from the yellow areas of the variegated foliage are near and through Green Group 137A, 137B, and 137C near the midrib to near and through Yellow-Green Group 147A. The variegated areas range from Yellow Group 8C, Yellow Groups 12A, to near and through Yellow Group 13A. The midrib is Yellow Group 2C. Under (Dorsal) Surface: The all green leaves and the distinctly green areas most distance from the yellow areas of variegated foliage are near and through Yellow-Green Group 144A. The variegated areas are near and through Yellow-Green Group 143C, Yellow-Green Group 144A, and Yellow-Green Group 153B to 153D nearest the yellow areas. The yellow areas are near and through Yellow-Orange Group 14C, Yellow-Orange Group 15C, and Yellow-Orange Groups 16B.

*Petioles.*—Color: Five Year-Old Plant: Range near and through Yellow Group 9C and Yellow Group 10B. Two Year-Old Plant: The ventral surface displays Greyed-Purple Group 186A to 186C, and the dorsal surface displays Greyed-Purple Group 187A to 187B.

*Stems.*—Color: Five Year-Old Plant: The current season's growth ranges from Greyed-Orange Group 165B to 165C to Greyed-Red Group 180C, 181D, 182B to 182C to Greyed-Brown Group 199B to 199C. Older stems of 2 to 4 years display Greyed-Green Group 197A and near and through Grey Group 201A. Two Year-Old Plant: The current season's growth ranges from Red-Purple Group 59A and 71A through Purple Group 79A to 79C. Older stems of 2 years display areas of Greyed-Green Group 197A to near and through Grey Group 201A.

Inflorescence:

*Type.*—Axillary, usually solitary to rarely with 2- or 3-flowered cymes.

*Bearing.*—On current season's growth.

*Time.*—Commonly mid- to late-May to early-June.

*Size.*—Approximately 4 mm in diameter.

*Petal color.*—Dull green-white, Green-White Group 157B at first opening, and Green-White Group 157C to 157D and White Group 155C at petal drop.

*Petal number.*—Commonly 4, and very rarely 5.

*Petal shape.*—Ovate.

*Pistil.*—One per flower. The plant dioecious for all practical purposes and bears flowers that are only female functional.

*Stamen.*—Four in number, and do not project beyond the corolla with rudimentary anthers. The male parts are non-funtional.

*Fragrance.*—None observed.

*Peduncle.*—Approximately 3.8 mm in length on average.

*Fruit.*—None observed.

Disease resistance: No special susceptibility or resistance to common Ilex diseases or pests has been observed to date under commercial growing conditions and when grown in unsprayed areas.

The new 'Drops of Gold' variety has not been observed under all possible environmental conditions to date. Thus, it possible that some variation in phenotypic expression may be displayed under different light intensity and duration and different cultural conditions.

I claim:

1. A new and distinct Japanese Holly plant having the following combination of characteristics:

(a) when exposed to full sun during formation the foliage is dark glossy green with irregular bright golden yellow variegation that is absent in the parent 'Hetzii' variety, (b) exhibits an attractive broad upright spreading growth habit, (c) forms dioecious female functional flowers, and, (d) has proven to be hardy in U.S.D.A. Hardiness Zone No. 6A;

substantially as herein shown and described.

* * * * *

*Ilex crenata* 'Drops of Gold' FIG. 1

*Ilex crenata* 'Drops of Gold' FIG. 2

*Ilex crenata* 'Drops of Gold'

*Ilex crenata* 'Drops of Gold'